US00PP10124P

United States Patent [19]

Kleinhanns

[11] Patent Number: Plant 10,124

[45] Date of Patent: Nov. 18, 1997

[54] DAHLIA PLANT NAMED BAPUR

[75] Inventor: Christoph Kleinhanns, Eisleben, Germany

[73] Assignee: Saatzucht Quedlinburg GmbH, Quedlinburg, Germany

[21] Appl. No.: 657,649

[22] Filed: Jun. 3, 1996

[51] Int. Cl.[6] ..... A01H 5/00

[52] U.S. Cl. ..... Plt./87.8

[58] Field of Search ..... Plt./87.8

*Primary Examiner*—James R. Feyrer
*Assistant Examiner*—Melissa L. Kimball
*Attorney, Agent, or Firm*—C. A. Whealy

[57] ABSTRACT

A distinct cultivar of Dahlia plant named Bapur, characterized by its compact growth habit; small leaves and inflorescences that are proportional to the overall plant size; ease of propagation; and red purple ray florets with bright yellow disc florets.

2 Drawing Sheets

The present invention relates to a new and distinct cultivar of Dahlia plant, botanically known as *Dahlia hybrida*, and hereinafter referred to by the cultivar name Bapur.

The new Dahlia is a product of a planned breeding program conducted by the inventor in Quedlinburg, Germany. The objective of the breeding program was to create new Dahlia cultivars having a compact growth habit suitable for 7 to 9-cm container production, small inflorescences, desirable inflorescence colors, and inflorescences and foliage with good substance.

The new Dahlia originated from a cross made by the inventor of the inventor's proprietary Dahlia seedling selections. The cultivar Bapur was discovered and selected by the inventor as a flowering plant within the progeny of this cross in a controlled environment in Quedlinburg, Germany.

Asexual reproduction of the new Dahlia by terminal cuttings taken at Quedlinburg, Germany, has shown that the unique features of this new Dahlia are stable and reproduced true to type in successive generations.

The following traits have been repeatedly observed and are determined to be the unique characteristics of Bapur. These characteristics in combination distinguish Bapur as a new and distinct cultivar:

1. Compact growth habit, suitable for 7 to 9-cm containers. Plants do not require growth retardants.
2. Small leaves and inflorescences that are proportional to the overall plant size.
3. Excellent rooting and easy to propagate.
4. Red purple ray florets with bright yellow disc florets.

The new Dahlia has not been observed under all possible environmental conditions. The phenotype may vary somewhat with variations in environment such as temperature, daylength and light intensity, without, however, any variance in genotype.

Compared to the female parent, plants of the new Dahlia have smaller inflorescences. Plants of the new Dahlia differ from the male parent in ray floret color.

Plants of the new Dahlia are similar to the cultivar Betty (disclosed in U.S. Plant Pat. No. 7,762) in ray floret color. However, in side-by-side comparisons conducted in Quedlinburg, Germany, under commercial practice, plants of the new Dahlia differed from plants of the cultivar Betty in the following characteristics:

1. Plants of the new Dahlia are more compact and shorter than plants of the cultivar Betty.
2. Leaves of plants of the new Dahlia are smaller than leaves of plants of the cultivar Betty.
3. Inflorescences of plants of the new Dahlia are smaller than inflorescences of plants of the cultivar Betty.

BRIEF DESCRIPTION OF THE DRAWINGS

The accompanying colored photographs illustrate the overall appearance of the new cultivar, showing the colors as true as it is reasonably possible to obtain in colored reproductions of this type.

The upper photograph on the first sheet of photographs comprises a top perspective view of a typical flowering plant of Bapur.

The lower photograph comprises a top perspective view of immature (top) and mature (bottom) leaves. The upper (left) and under (right) sides of the leaves are shown.

The upper photograph on the second sheet of photographs comprises a top perspective view of a developing inflorescence showing the upper (left) and under (right) sides of the inflorescence.

The lower photograph comprises a top perspective view of developing (left) and fully developed (right) inflorescences. The floret and foliage colors in these photographs appear different than the actual colors due to light reflectance.

In the following description, color references are made to The Royal Horticultural Society Colour Chart except where general terms of ordinary dictionary significance are used. The following observations and measurements describe plants grown in Quedlinburg, Germany, during the winter season under commercial practice in a glass-covered greenhouse with average night temperatures of 15C, average day temperatures of 20C, and light levels of 2,500 lux.

Botanical classification: Dahlia hybrida cultivar Bapur.
Commercial classification: Pot Dahlia.
Parentage:
- *Male, or pollen, parent.*—Proprietary Dahlia seedling selection.
- *Female, or seed, parent.*—Proprietary Dahlia seedling selection.

Propagation:
- *Type.*—Terminal tip cuttings.
- *Time to rooting.*—15 to 20 days with soil temperatures of 20C.
- *Rooting habit.*—Propagates easily, roots fibrous and well-branched.

Plant description:
- *Appearance.*—Perennial herbaceous potted plant. Bushy with stems upright. Freely branching, plants do not require pinching. Compact growth habit and moderate growth rate. Suitable for 7 to 9-cm containers. From a rooted cutting, six weeks are required to produce a flowering pot plant.

*Plant height.*—About 17 cm.

*Stem description.*—Internode length: 1.5 to 3 cm. Diameter: 3 to 4 mm. Color: 144A.

*Foliage description.*—Arrangement: Young foliage: Single. Fully expanded: Compound, trifoliate. Leaf size: Young foliage: Length: About 4 cm. Width: About 3 cm. Mature foliage: Length: About 10 cm. Width: About 6 cm. Leaf/leaflet shape: Ovate. Leaf/leaflet apex: Acuminate. Leaf/leaflet base: Attenuate. Leaf/leaflet margin: Serrated. Leaf/leaflet texture: Smooth, glabrous. Petiole length: Young foliage: About 1.5 cm. Fully expanded: About 3 cm. Color: Young foliage upper surface: Darker than 137A. Young foliage under surface: 138B/138C. Fully expanded foliage upper surface: Darker than 137A. Fully expanded foliage under surface: 138B/138C. Petiole: 144B.

Flowering description:

*Appearance.*—Daisy Inflorescence form. Inflorescences borne on terminals above foliage, arising from leaf axils. Disc and ray florets arranged acropetally on a capitulum.

*Flowering reponse.*—Under natural conditions, plants flower continuous in the summer/autumn in the Northern Hemisphere. At other times of the year, inflorescence initiation and development can be induced under long day/short night conditions (less than 11 hours of darkness). Inflorescences persistent.

*Inflorescence size.*—Diameter: 3.5 to 4 cm. Depth (height): 2 to 2.5 cm.

*Flower bud.*—Shape: Ovoid. Size: Length: 5 to 8 mm. Diameter: 7 to 10 mm. Color: 144B.

*Ray florets.*—Shape: Oblanceolate. Size: Length: About 15 min. Width: 5 to 7 mm. Apex: Obtuse. Margin: Entire. Texture: Satiny, smooth and glabrous. Number of ray florets per inflorescence: About 40, three to four rows of florets. Color: Upper surface: Distal: 67B. Proximal: 61A/61B. Under surface: Distal: 68A. Proximal: 67B/67C.

*Disc florets.*—Number of disc florets per inflorescence: About 30. Color: 14B.

*Peduncle.*—Aspect: Erect and strong. Length: 3 to 5 cm. Diameter: About 1 min. Texture: Glabrous. Color: 144B.

*Sepals.*—Quantity per inflorescence: 5. Shape: Oblanceolate. Tip: Acute. Marin: Entire. Color: 137A.

*Reproductive organs.*—Androecium: Anther size: About 2 mm. Anther color: 14B. Pollen: 14B. Gynoecium: Not present on all ray florets. Style length: About 2 mm. Style color: 14B. Stigma color: 14B.

Disease resistance: No known Dahlia diseases observed to date on plants grown under commercial greenhouse conditions.

Seed production: Seed production has not been observed.

It is claimed:

1. A new and distinct cultivar of Dahlia plant named Bapur, as illustrated and described.

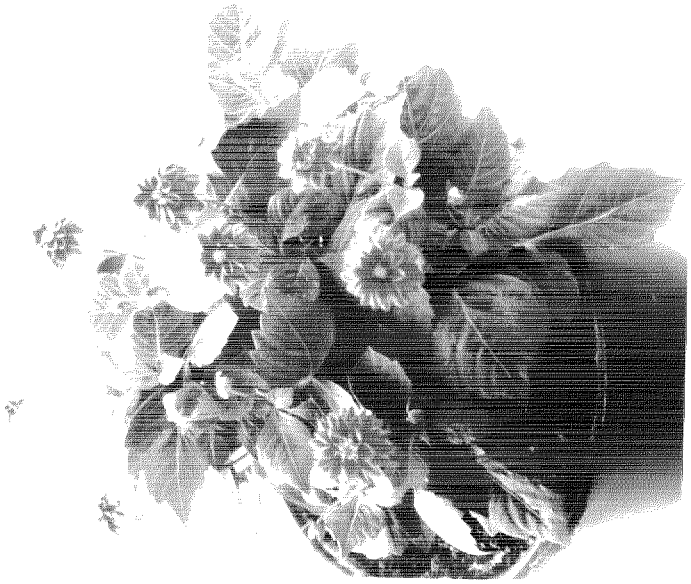
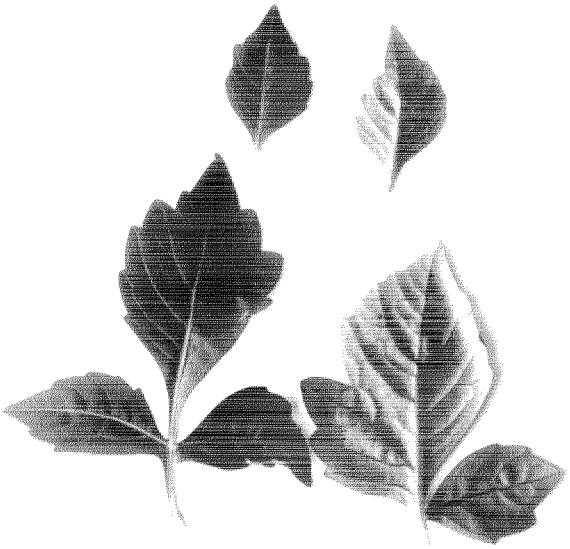

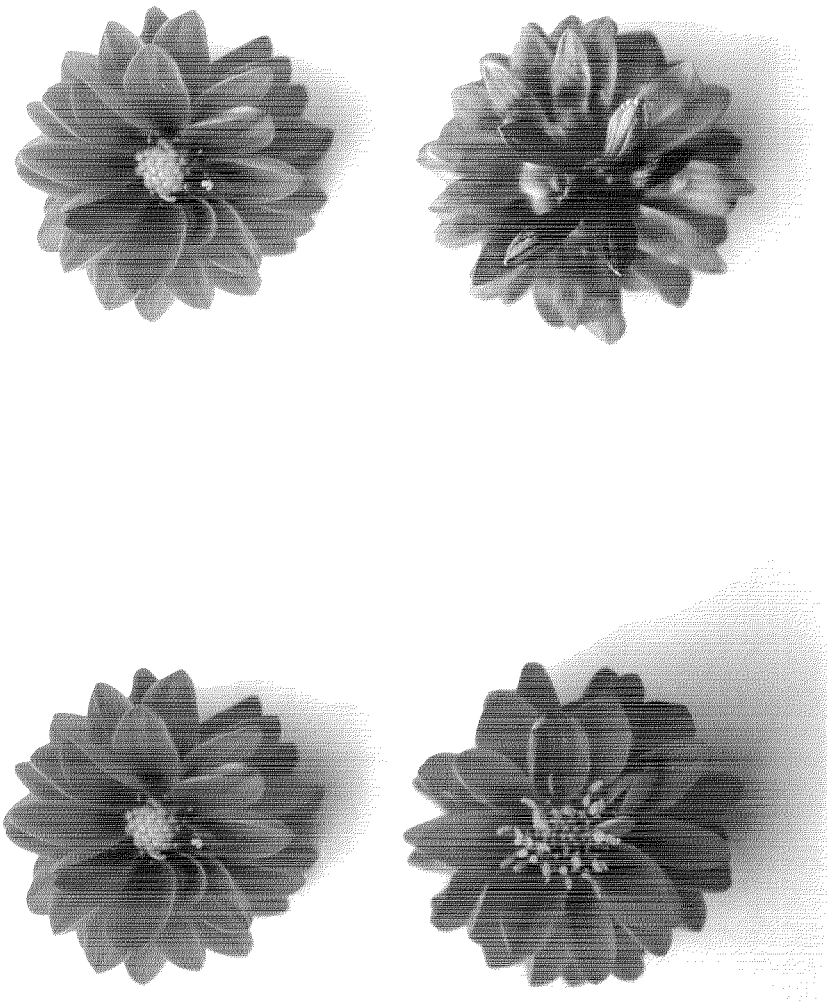

* * * * *